United States Patent
Kobayashi et al.

(10) Patent No.: US 8,952,044 B2
(45) Date of Patent: Feb. 10, 2015

(54) ANTIMYCOTIC PHARMACEUTICAL COMPOSITION

(75) Inventors: Hirokazu Kobayashi, Yokohama (JP); Nobuo Kubota, Yokohama (JP)

(73) Assignees: Pola Pharma Inc., Shinagawa-ku, Tokyo (JP); Nihon Nohyaku Co., Ltd., Chuo-ku, Tokyo (JP)

( * ) Notice: Subject to any disclaimer, the term of this patent is extended or adjusted under 35 U.S.C. 154(b) by 84 days.

(21) Appl. No.: 13/389,071

(22) PCT Filed: Jul. 29, 2010

(86) PCT No.: PCT/JP2010/063230
§ 371 (c)(1),
(2), (4) Date: Feb. 6, 2012

(87) PCT Pub. No.: WO2011/024620
PCT Pub. Date: Mar. 3, 2011

(65) Prior Publication Data
US 2012/0149745 A1    Jun. 14, 2012

(30) Foreign Application Priority Data
Aug. 25, 2009    (JP) .................................. 2009-194835

(51) Int. Cl.
| A01N 43/10 | (2006.01) |
| A01N 25/00 | (2006.01) |
| A61K 31/4178 | (2006.01) |
| A61K 9/00 | (2006.01) |
| A61K 47/08 | (2006.01) |

(52) U.S. Cl.
CPC ........... *A61K 31/4178* (2013.01); *A61K 9/0014* (2013.01); *A61K 47/08* (2013.01)
USPC ......................................... 514/397; 424/404

(58) Field of Classification Search
USPC ............................................ 514/397; 424/61
See application file for complete search history.

(56) References Cited

U.S. PATENT DOCUMENTS

| 4,267,169 | A | 5/1981 | Kamishita et al. |
| 4,636,520 | A | 1/1987 | Umio et al. |
| 4,764,381 | A | 8/1988 | Bodor et al. |
| 5,340,836 | A | 8/1994 | Reinhard et al. |
| 5,461,068 | A | 10/1995 | Thaler et al. |
| 5,690,923 | A | 11/1997 | De Vringer et al. |
| 5,753,256 | A | 5/1998 | Cordes et al. |
| 5,814,305 | A | 9/1998 | Laugier et al. |
| 5,900,488 | A | * 5/1999 | Kodama et al. ............ 548/315.1 |
| 5,962,536 | A | 10/1999 | Komer |
| 5,993,787 | A | 11/1999 | Sun et al. |
| 6,007,791 | A | 12/1999 | Coombes et al. |
| 6,008,256 | A | 12/1999 | Haraguchi et al. |
| 6,017,920 | A | 1/2000 | Kamishita et al. |
| 6,083,518 | A | 7/2000 | Lindahl |
| 6,428,654 | B1 | 8/2002 | Cronan, Jr. et al. |
| 6,585,963 | B1 | 7/2003 | Quan et al. |
| 6,740,326 | B1 | 5/2004 | Meyer et al. |
| 2003/0017207 | A1 | 1/2003 | Lin et al. |
| 2003/0235541 | A1 | 12/2003 | Maibach et al. |
| 2004/0208906 | A1 | 10/2004 | Tatara et al. |
| 2005/0232879 | A1 | 10/2005 | Sasagawa et al. |
| 2006/0140984 | A1 | 6/2006 | Tamarkin et al. |
| 2007/0099932 | A1 | 5/2007 | Shirouzu et al. |
| 2008/0031835 | A1 | 2/2008 | Kawamura et al. |

(Continued)

FOREIGN PATENT DOCUMENTS

| EP | 0 070 525 | 1/1983 |
| EP | 0 440 298 | 8/1991 |

(Continued)

OTHER PUBLICATIONS

Luliconazole structure, Product portpolio, Viwit, retrieved from website http://www.viwit.com/en_us/product_detail/187164-19-8.html, on Oct. 31, 2014.*
Vieira, et al. "Cationic Lipids and Surfactants as Antifungal Agents: Mode of Action," *Journal of Antimicrobial Chemotherapy*, Vo. 58, pp. 760-767, 2006.
SDS Density downloaded from www.chemicalbook.com/ChemicalProductProperty_EN_CB2147453.htm, 2 pages, copyright 2010.
Pluronics Density downloaded from www.chemicalbook.com/ChemicalProductPropertyEN_Cb2709101.htm, 2 pages, copyright 2010.
Ethyl Cellulose Density downloaded from www.chemicalbook.com/ProductMSDSDetailCB6165620_EN.htm, 3 pages, copyright 2008.
Database WPI Week 200732, AN 2007-337919 and JP 2007-091661.
International Search Report dated Oct. 18, 2010 issued to international application No. PCT/JP2010/063230.

(Continued)

*Primary Examiner* — Ernst V Arnold
*Assistant Examiner* — Kyung Sook Chang
(74) *Attorney, Agent, or Firm* — Knobbe, Martens, Olson & Bear LLP

(57) ABSTRACT

A pharmaceutical composition which comprises 1) a compound represented by the following general formula (1) and/or a salt thereof; and 2) a ketone such as methyl ethyl ketone. Preferably, the compound represented by the following general formula (1) is luliconazole, where $R_1=R_2=$a chlorine atom: where $R_1$ and $R_2$ each independently represents a hydrogen atom or a halogen atom, and at least one of $R_1$ and $R_2$ represents a halogen atom. The present invention provides a preparation excellent in solubilization stability for a compound represented by the general formula (1) and/or a salt thereof in low-temperature or high-temperature storage.

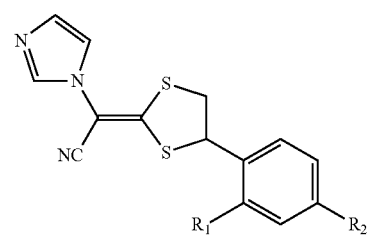

(1)

6 Claims, No Drawings

(56) References Cited

U.S. PATENT DOCUMENTS

| | | | |
|---|---|---|---|
| 2008/0260656 A1 | 10/2008 | Mallard | |
| 2009/0030059 A1 | 1/2009 | Miki et al. | |
| 2009/0076109 A1 | 3/2009 | Miki et al. | |
| 2009/0099202 A1 | 4/2009 | Shirouzu et al. | |
| 2009/0137651 A1 | 5/2009 | Kobayashi et al. | |
| 2009/0202602 A1 | 8/2009 | Ishima et al. | |
| 2010/0168200 A1 | 7/2010 | Masuda et al. | |
| 2010/0173965 A1 | 7/2010 | Masuda et al. | |
| 2010/0204293 A1 | 8/2010 | Masuda et al. | |
| 2010/0210702 A1* | 8/2010 | Vontz et al. | 514/397 |
| 2010/0210703 A1 | 8/2010 | Vontz et al. | |
| 2012/0014893 A1 | 1/2012 | Kobayashi et al. | |
| 2012/0022120 A1 | 1/2012 | Kobayashi et al. | |
| 2013/0011351 A2 | 1/2013 | Kobayashi et al. | |
| 2013/0090365 A1 | 4/2013 | Kubota et al. | |
| 2014/0080882 A1 | 3/2014 | Masuda et al. | |

FOREIGN PATENT DOCUMENTS

| | | |
|---|---|---|
| EP | 0715856 | 6/1996 |
| EP | 1 138 314 | 10/2001 |
| EP | 1 522 316 | 4/2005 |
| EP | 1 637 132 | 3/2006 |
| EP | 2 005 958 | 12/2008 |
| EP | 2 005 959 | 12/2008 |
| EP | 2 025 337 | 2/2009 |
| EP | 2 191 827 | 6/2010 |
| EP | 1 537 868 | 8/2011 |
| JP | 61-118315 | 6/1986 |
| JP | 62-093227 | 4/1987 |
| JP | 62-223163 | 10/1987 |
| JP | 01-242525 | 9/1989 |
| JP | 1-242525 | 9/1989 |
| JP | 01-246219 | 10/1989 |
| JP | 02-264723 | 10/1990 |
| JP | 02-275877 | 11/1990 |
| JP | 05-306223 | 11/1993 |
| JP | 06-199701 | 7/1994 |
| JP | 06-211651 | 8/1994 |
| JP | 07-188027 | 7/1995 |
| JP | 7-74144 | 8/1995 |
| JP | 07-206711 | 8/1995 |
| JP | 07-223971 | 8/1995 |
| JP | 08-020527 | 1/1996 |
| JP | 08-291049 | 11/1996 |
| JP | 10-152433 | 6/1998 |
| JP | 10-226639 | 8/1998 |
| JP | 10-226686 | 8/1998 |
| JP | 2001-064206 | 3/2001 |
| JP | 2001-316247 | 11/2001 |
| JP | 2002-114680 | 4/2002 |
| JP | 2002-193755 | 7/2002 |
| JP | 2002-284702 | 10/2002 |
| JP | 2002-363070 | 12/2002 |
| JP | 2003-252798 | 9/2003 |
| JP | 2004-529923 | 9/2004 |
| JP | 2005-154306 | 6/2005 |
| JP | 2005-239678 | 9/2005 |
| JP | 2005-289879 | 10/2005 |
| JP | 2005-298388 | 10/2005 |
| JP | 2005-298635 | 10/2005 |
| JP | 2006-028123 | 2/2006 |
| JP | 2006-232856 | 9/2006 |
| JP | 2006-306734 | 11/2006 |
| JP | 2007-091661 | 4/2007 |
| JP | 2007-091661 A | 4/2007 |
| JP | 2009-511553 | 3/2009 |
| RU | 2 270 894 C2 | 3/2004 |
| WO | WO 90/14094 | 11/1990 |
| WO | WO 95/30440 | 11/1995 |
| WO | WO 96/11710 | 4/1996 |
| WO | WO 96/40047 | 12/1996 |
| WO | WO 97/02821 | 1/1997 |
| WO | WO 97/07794 | 3/1997 |
| WO | WO 00/01384 | 1/2000 |
| WO | WO 02/062336 | 8/2002 |
| WO | WO 02/083084 | 10/2002 |
| WO | WO 02/087570 | 11/2002 |
| WO | WO 03/020248 | 3/2003 |
| WO | WO 03/105841 | 12/2003 |
| WO | WO 2004/021968 | 3/2004 |
| WO | WO 2004/084826 | 10/2004 |
| WO | WO 2004/091521 | 10/2004 |
| WO | WO 2005/099764 | 10/2005 |
| WO | WO 2005/123136 | 12/2005 |
| WO | WO 2006/038317 | 4/2006 |
| WO | WO 2007/042682 | 4/2007 |
| WO | WO 2007/102241 | 9/2007 |
| WO | WO 2007/102242 | 9/2007 |
| WO | WO 2007/077806 | 12/2007 |
| WO | WO 2008/075207 | 6/2008 |
| WO | WO 2009031642 A1 * | 3/2009 |
| WO | WO 2010/093992 | 8/2010 |
| WO | WO 2014/041708 A1 | 3/2014 |
| WO | WO 2014/041825 A1 | 3/2014 |
| WO | WO 2014/041846 A1 | 3/2014 |
| WO | WO 2014/042043 A1 | 3/2014 |
| WO | WO 2014/136282 | 9/2014 |

OTHER PUBLICATIONS

Absolute ethanol MSDS (www.sciencelab.com/msds.php?msdsId=9923955) 7 pages.
Borrás-Blasco, et al. "A Mathematical Approach to Predicting the Percutaneous Absorption Enhancing Effect of Sodium Lauryl Sulphate," International Journal of Pharmaceutics, vol. 269, pp. 121-129, 2004.
Costa Martins, et al "In vitro Sensitivity of Dermatophytes to Urea," Clinics, vol. 61, No. 1, pp. 9-14, 2006.
Crotamiton Properties (http://www.chemspider.com/Chemical-Structure.2780.html) 2 pages.
GHS Classification Guidance for Enterprises (2nd Edition, Ministry of Economy, Trade and Industry, Japan, Mar. 2010.
International Search Report dated Oct. 15, 2010 issued to international application No. PCT?JP2010/056884.
International Search Report dated Oct. 18, 2010 issued to international application No. PCT/JP2010/056881.
Methyl Ethyl Ketone MSDS (www.sciencelab.com/msds.php?msdsId=9927358) 6 pages, (2005).
Niwano, et al. "Efficacy of NND-502, a Novel Imidazole Antimycotic Agent, in Experimental Models of *Candida albicans* and *Aspergillus fumigatus* Infections," International journal of Antimicrobial Agents, vol. 12, pp. 221-228, 1999.
Niwano, et al. "In vitro and In vivo Antidermatophyte Activities of NND-4502, a Novel Optically Active Imidazole Antimycotic Agent," Antimicrobial Agents and Chemotherapy, vol. 42, No. 4, pp. 967-970, Apr. 1998.
Niwano, et al. "Lanoconazole and Its Related Optically Active Compound NND-502: Novel Antifungal Imidazoles with a Ketene Dithioacetal Structure," Current Medicinal Chemistry, vol. 2, pp. 147-160, 2003.
Uchida, et al. "In vitro Activity of Novel Imidazole Antifungal Agent NND-502 Against Malassezia Species," International Journal of Antimicrobial Agents, vol. 21, pp. 234-238, 2003.
Uchida, et al. "In vitro Antifungal Activity of Luliconazole (NND-502), a Novel Imidazole Antifungal Agent," Journal of Infectious Chemothererapy, vol. 10, pp. 216-219, 2004.
www.babymd.com (available online as of Feb. 16, 2001 as evidenced by the attached Internet Archive report) accessed online Dec. 18, 2010.
Koga et al., "In vitro antifungal activities of luliconazole, a new topical imidazole," Med. Mycol., vol. 47(6), pp. 640-647 (2009).
U.S. Appl. No. 14/263,293, Masuda et al.

* cited by examiner

ANTIMYCOTIC PHARMACEUTICAL COMPOSITION

CROSS-REFERENCE TO RELATED APPLICATIONS

This application is the U.S. National Phase under 35 U.S.C. §371 of International Application PCT/JP2010/063230, filed Jul. 29, 2010, which claims priority to JP Application No. 2009-194835, filed Aug. 25, 2009.

TECHNICAL FIELD

The present invention relates to a pharmaceutical composition, and more specifically, to a pharmaceutical composition, which is useful as an antimycotic agent.

BACKGROUND ART

A compound having a structure represented by the general formula (1), such as luliconazole (in the general formula (1), $R_1=R_2=$chlorine atom), has excellent antimycotic activity, and it has been suggested that the compound may be applied to a treatment for a mycosis of the nail, which has been considered to be untreatable by external application (e.g., see Patent Document 1). Such preparation for treating the mycosis of the nail is desired to have an increased content of the compound represented by the general formula (1). However, because of its high crystallinity, solvents which can be used for producing a preparation containing the compound at a high concentration are very limited. That is, some solvents may cause disadvantages such as crystallization under a low temperature condition (such as 5° C.) and crystallization by application. In addition, in a solution of a compound represented by the general formula (1) which has stereoisomers, such as luliconazole, an stereoisomer such as an SE form is easily formed in some cases, and as solvents capable of preventing formation of such stereoisomers, only crotamiton, propylene carbonate, and N-methyl-2-pyrrolidone are known (e.g., see Patent Document 2). However, in some cases, blending of such solvents is restricted because of drug efficacy of the solvents, such as the anti-inflammatory effect of the solvents, and it has been desired to develop a novel solvent for a preparation of luliconazole or the like which substitutes for the solvents. In particular, in the case of a liquid preparation, the pharmacological effect significantly decreases by crystallization or the like, and hence such solubilization technology is an important factor for formulation. In addition, there may be a situation where a stereoisomer such as a Z form should be considered.

Lanoconazole (in the general formula (1), $R_1=$hydrogen atom, and $R_2=$chlorine atom), which is a compound represented by the general formula (1), is known as a useful antimycotic agent. However, also in the case of the compound, there are large problems in production technologies, such as crystallization caused by using the compound at a low temperature and decrease in the content caused by storage at a high temperature.

On the other hand, a ketone such as methyl ethyl ketone is widely used as a solvent excellent in solubilization ability. However, there is no known pharmaceutical preparation containing 1) a compound represented by the following general formula (1) and/or a salt thereof and 2) a ketone represented by the general formula (2).

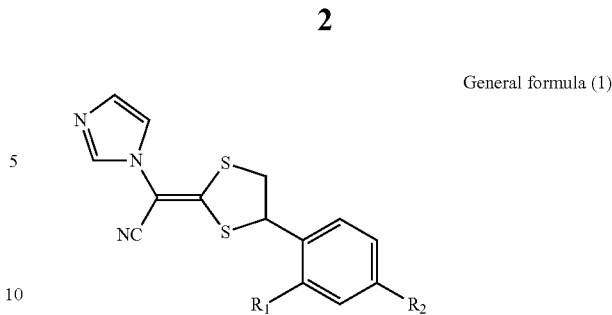

General formula (1)

(In the formula, $R_1$ and $R_2$ each independently represents a hydrogen atom or a halogen atom, and at least any one of $R_1$ and $R_2$ represents a halogen atom.)

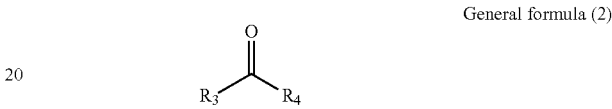

General formula (2)

(In the formula, $R_3$ and $R_4$ each independently represents an alkyl group or alkenyl group which may have an aromatic group, or an aromatic group, and the sum of the number of carbon atoms in $R_3$ and $R_4$ is 3 or more.)

Further, a hydroxyalkylbenzene such as benzyl alcohol or phenethyl alcohol is widely used as a solvent for solubilizing poorly-soluble components in the drug or quasi-drug field (e.g., see Patent Document 3). However, there is no example of the use of the hydroxyalkylbenzene for solubilization of the compound represented by the general formula (1) and/or the salt thereof. Moreover, there is no example of the use of the hydroxyalkylbenzene as a solvent for solubilization in a pharmaceutical composition containing the compound or the like and the ketone represented by the general formula (2).

[Patent Document 1] WO/2007/102241
[Patent Document 2] WO/2007/102242
[Patent Document 3] JP 2006-232856 A

SUMMARY OF INVENTION

Technical Problem

The present invention has been made in view of the above-mentioned circumstances, and an object of the present invention is to provide a preparation excellent in solubilization stability for a compound represented by the general formula (1) and/or a salt thereof in low-temperature or high-temperature storage.

Solution to Problems

In consideration of the above-mentioned circumstances, the inventors of the present invention have made intensive studies and efforts in search of a preparation component which has an effect of enhancing solubilization stability of the compound represented by the general formula (1) and/or the salt thereof and is capable of substituting for crotamiton, propylene carbonate, or N-methyl-2-pyrrolidone. As a result, the inventors have finally completed the invention by finding out that a ketone represented by the general formula (2), such as methyl ethyl ketone, has such properties. In other words, the present invention is as follows.

[1] A pharmaceutical composition comprising: 1) a compound represented by the following general formula (1) and/or a salt thereof; and 2) a ketone represented by the following general formula (2):

General formula (1)

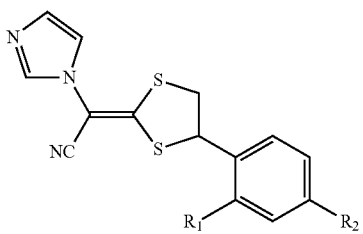

where $R_1$ and $R_2$ each independently represents a hydrogen atom or a halogen atom, and at least one of $R_1$ and $R_2$ represents a halogen atom; and General formula (2)

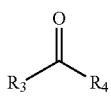

where $R_3$ and $R_4$ each independently represents an alkyl group or alkenyl group which may have an aromatic group, or an aromatic group, and a sum of a number of carbon atoms in $R_3$ and $R_4$ is 3 or more.

[2] The pharmaceutical composition according to [1], wherein the compound represented by the general formula (1) is luliconazole, where $R_1=R_2=$a chlorine atom.

[3] The pharmaceutical composition according to [1] or [2], wherein the ketone represented by the general formula (2) is methyl ethyl ketone, methyl isobutyl ketone, or benzophenone.

[4] The pharmaceutical composition according to any one of [1] to [3], further comprising a hydroxyalkylbenzene.

[5] The pharmaceutical composition according to [4], wherein the hydroxyalkylbenzene is benzyl alcohol.

[6] The pharmaceutical composition according to any one of [1] to [5], further comprising an α-hydroxy acid and/or phosphoric acid.

[7] The pharmaceutical composition according to any one of [1] to [6], which is a drug for treating tinea unguium.

[8] A method of producing a pharmaceutical composition comprising: 1) a compound represented by the following general formula (1) and/or a salt thereof; 2) a ketone represented by the following general formula (2); and 3) a hydroxyalkylbenzene, the method comprising: mixing, as a solubilizing agent, the hydroxyalkylbenzene with the compound represented by the general formula (1) and/or the salt thereof; and mixing, as a dilution medium, the ketone represented by the general formula (2) with the resultant mixture:

General formula (1)

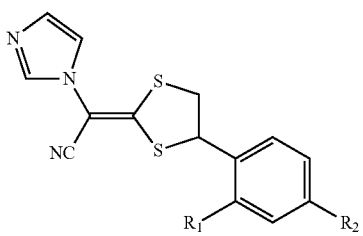

where $R_1$ and $R_2$ each independently represents a hydrogen atom or a halogen atom, and at least one of $R_1$ and $R_2$ represents a halogen atom; and General formula (2)

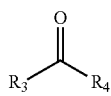

where $R_3$ and $R_4$ each independently represents an alkyl group or alkenyl group which may have an aromatic group, or an aromatic group, and a sum of a number of carbon atoms in $R_3$ and $R_4$ is 3 or more.

Advantageous Effects of Invention

According to the present invention, it is possible to provide a preparation excellent in solubilization stability for the compound represented by the general formula (1) and/or the salt thereof in low-temperature or high-temperature storage.

DESCRIPTION OF EMBODIMENTS

<1> Essential Component of Pharmaceutical Composition of the Present Invention: Compound Represented by General Formula (1) and/or Salt Thereof.

A pharmaceutical composition of the present invention contains a compound represented by the general formula (1), such as luliconazole or lanoconazole, and/or a salt thereof. Luliconazole is a compound having a chemical name of (R)-(−)-(E)-[4-(2,4-dichlorophenyl)-1,3-dithiolan-2-ylidene]-1-imidazolylacetonitrile, and lanoconazole is a compound having a chemical name of (±)-(E)-[4-(2-chlorophenyl)-1,3-dithiolan-2-ylidene]-1-imidazol ylacetonitrile. Methods of producing such compounds have been known (for example, JP 09-100279 A).

The pharmaceutical composition of the present invention contains the compound represented by the general formula (1) and/or the salt thereof at a concentration of usually 0.5 to 20% by mass, or preferably 1 to 10% by mass with respect to the total amount of the pharmaceutical composition. The compound represented by the general formula (1), such as luliconazole, and/or the salt thereof has high crystallinity. Therefore, even if crystallization is suppressed by adding a hydroxycarboxylic acid such as lactic acid, the compound and/or the salt thereof may cause crystallization when the compound and/or the salt thereof at a concentration of 4% by mass or more is stored at a low temperature (such as 5° C.). In the present invention, such crystallization is suppressed in a preparation containing the below-described ketone such as methyl ethyl ketone, and crystallization is further suppressed by a combination of preparations containing a hydroxyalkylbenzene and the ketone such as methyl ethyl ketone. In addition, in the case of a compound represented by the general formula (1), such as luliconazole, and/or a salt thereof, which has stereoisomers, the concentration of the compound serving as an active ingredient may decrease in high-temperature storage (such as 40° C.) because of stereoisomerization. In the present invention, such stereoisomerization is suppressed in the preparation containing the below-described ketone such as methyl ethyl ketone. The effect enhances the bioavailability of the preparation, in particular, transference into the nail, and hence enhances the therapeutic effect on tinea unguium. For a usual mycosis of the foot or a mycosis of the body, an enough effect is exerted by a treatment using a composition containing the compound represented by the general formula (1) and/or the salt thereof at a concentration of about 1 to 5% by mass. However, for a mycosis of the nail such as tinea unguium, a treatment using a pharmaceutical composition containing the compound represented by the general formula (1) and/or the salt thereof at a concentration of 5% by mass or more is required. In other words, the nail is an organ where transference into the tissue is difficult, and in order to transfer an effective amount of the composition, the content of the compound represented by the general formula (1) and/or the salt thereof is preferably 5% by mass or more, or more preferably 6% by mass or more with respect to the total amount of the pharmaceutical composition. In addition, in view of suppression of crystallization at low-temperature, the content is preferably 10% by mass or less. In view of the foregoing, the content in a pharmaceutical composition for the nail is preferably about 6 to 10% by mass.

The above-mentioned "salt thereof" is not particularly limited as long as the salt is physiologically acceptable. Preferred examples of the salt include: mineral acid salts such as a hydrochloride, a nitrate, a sulfate, and a phosphate; organic acid salts such as a citrate, an oxalate, a glycolate, a lactate, and an acetate; and sulfuric acid-containing salts such as a mesilate and a tosilate. Of those, the mineral acid salts such as the phosphate and the α-hydroxy acid salts such as the glycolate and the lactate are particularly preferred.

<2> Essential Component of Pharmaceutical Composition of the present invention: ketone represented by general formula (2)

The pharmaceutical composition of the present invention contains the ketone represented by the general formula (2) as an essential component. In the ketone represented by the general formula (2), $R_3$ and $R_4$ each independently represents an alkyl group or alkenyl group which may have an aromatic group, or an aromatic group, and the sum of the number of carbon atoms in $R_3$ and $R_4$ is 3 or more. In terms of a solvent property to solubilize the compound represented by the general formula (1), the number of the carbon atoms in the substituents $R_3$ and $R_4$ is usually 15 or less, or preferably 13 or less.

Examples of the alkyl group which may have an aromatic group include a methyl group, an ethyl group, a propyl group, an isopropyl group, a butyl group, an isobutyl group, and a benzyl group.

Examples of the alkenyl group which may have an aromatic group include a butenyl group.

Examples of the aromatic group include a phenyl group.

Specific preferred examples of the ketone include methyl ethyl ketone, diethyl ketone, methyl propyl ketone, methyl isopropyl ketone, methyl isobutyl ketone, ethyl propyl ketone, propyl butyl ketone, and benzophenone. Of those, methyl ethyl ketone, methyl isobutyl ketone, and benzophenone are particularly preferred. This is because such ketones each has excellent ability to suppress formation of a stereoisomer in high-temperature storage while the ketones each dissolves the compound represented by the general formula (1) and/or the salt thereof at a high concentration. Such ketones represented by the general formula (2) may be products which are usually commercially available as solvents, and one kind of the ketones may be used alone, or two or more kinds of them may be used in combination.

The content of the ketone is, for example, 5 to 99% by mass, or preferably 10 to 80% by mass in total with respect to the total amount of the pharmaceutical composition. In addition, the content ratio (mass ratio) of the compound represented by the general formula (1) and/or the salt thereof and the ketone represented by the general formula (2) is usually 1:200 to 1:0.1, preferably 1:150 to 1:0.5, or more preferably 1:100 to 1:0.6.

It is preferred that the compound represented by the general formula (1) and/or the salt thereof, or preferably the salt is solvated with the below-mentioned hydroxyalkylbenzene, and then the ketone represented by the general formula (2) is gradually added to the solution with stirring to solubilize the compound represented by the general formula (1) and/or the salt thereof as a dilution medium. According to such production method, a highly-concentrated preparation can be obtained.

<3> Pharmaceutical Composition of the Present Invention

The pharmaceutical composition of the present invention contains the above-mentioned essential components and an optional component for formulation. Preferred examples of the optional component for formulation include: a lower alcohol such as ethanol or isopropanol; a higher alcohol such as isostearyl alcohol or oleyl alcohol; a polyvalent alcohol such as polyethylene glycol, glycerin, 1,3-butylene glycol, erythritol, sorbitol, xylitol, maltitol, gluconolactone, propylene glycol, dipropylene glycol, diglycerin, isoprene glycol, 1,2-pentanediol, 2,4-hexanediol, 1,2-hexanediol, 1,2-octanediol, polypropylene glycol, or 2-ethyl-1,3-hexanediol; a ketone such as acetone; a non-ionic surfactant such as a polyoxyethylene alkyl ether, a polyoxyethylene hardened castor oil, or a polyoxyethylene sorbitan fatty acid; a thickener such as hydroxypropyl cellulose or ethyl cellulose; a dibasic acid diester such as diethyl sebacate, dipropyl sebacate, or diethyl adipate; a hydroxyalkyl benzene such as benzyl alcohol, phenethyl alcohol, or phenyl propanol; a solvent such as an alkylene carbonate, for example, ethylene carbonate or propylene carbonate, N-methyl-2-pyrrolidone (hereinafter, referred to as "NMP"), or crotamiton; and a stabilizer such as an α-hydroxy acid, for example, lactic acid, glycolic acid, or citric acid, or a mineral acid, for example, phosphoric acid. Of those, the hydroxyalkylbenzene is particularly preferably contained because the compound acts together with the ketone represented by the general formula (2) to exert excellent effect of solubilizing the compound represented by the general formula (1) and/or the salt thereof and excellent effect of suppressing stereoisomerization of the compound and/or the salt thereof.

The alkyl group in the hydroxyalkylbenzene preferably has 1 to 4 carbon atoms, and specific preferred examples of such hydroxyalkylbenzene include benzyl alcohol, phenethyl alcohol, and phenyl propanol. One kind of the components may be contained alone, or two or more kinds of them may be used in combination. The hydroxyalkylbenzene is more preferably benzyl alcohol or phenethyl alcohol, or particularly preferably benzyl alcohol.

The component is contained in an amount of preferably 1 to 99% by mass, or more preferably 10 to 99% by mass in total with respect to the total amount of the pharmaceutical composition. If the component is contained at such content, it is possible to stabilize the dissolution state and to prevent crystallization when the compound represented by the general formula (1) and/or the salt thereof is stored at a low temperature, for example, at about 5° C. Moreover, the component exerts an effect of suppressing stereoisomerization of the compound represented by the general formula (1) and/or the salt thereof when stored at a high temperature of 40° C. or higher. In addition, the content ratio (mass ratio) of the ketone represented by the general formula (2) and the hydroxyalkylbenzene is usually 20:1 to 1:1, preferably 15:1 to 2:1, or more preferably 10:1 to 3:1. In particular, the hydroxyalkylbenzene suppresses crystallization at a low temperature, and hence the compound is preferably used as a solubilizing agent for the compound represented by the general formula (1) and/or the salt thereof. The pharmaceutical composition of the present invention is preferably produced using such solubilizing agent. The pharmaceutical composition of the present invention is preferably produced by solvating the compound represented by the general formula (1) and/or the salt thereof, or preferably the salt thereof, with the hydroxyalkylbenzene and adding the ketone represented by the general formula (2), such as methyl ethyl ketone, as a dilution medium with stirring to dissolve the compound and/or the salt.

In the present invention, the ketone represented by the general formula (2), such as methyl ethyl ketone, and a combination of the ketone and the hydroxyalkylbenzene, such as benzyl alcohol, may substitute for propylene carbonate, NMP, or crotamiton, and hence formulation can be performed without using the compounds. However, to supplement the technology of the effect of maintaining steric structure stability, preparations containing such compounds are also preferred. In addition, the preparations using such compounds fall within the technical scope of the present invention. In the case where the alkylene carbonate such as propylene carbonate, NMP, or crotamiton is contained, the content is preferably 1 to 30% by mass, or more preferably 2 to 15% by mass with respect to the total amount of the pharmaceutical composition.

Further, to improve the stability of the pharmaceutical composition of the present invention and the effect of suppressing crystallization after application, a stabilizer such as an α-hydroxy acid, for example, lactic acid, glycolic acid, or citric acid, or a mineral acid, for example, phosphoric acid is preferably contained at a concentration of preferably 0.1 to 20% by mass, or more preferably 1 to 10% by mass with respect to the total amount of the pharmaceutical composition. In addition, to improve the solubility and stability, a higher alcohol which is in a liquid form at 1 atm and 25° C., such as isostearyl alcohol, is preferably contained at a concentration of preferably 10 to 30% by mass, or more preferably 15 to 25% by mass. Moreover, to improve the solubility, a polyvalent alcohol such as propylene glycol is preferably contained at a concentration of preferably 1 to 30% by mass, or more preferably 5 to 20% by mass with respect to the total amount of the pharmaceutical composition.

The pharmaceutical composition of the present invention can be produced by treating such essential components and optional components in accordance with a conventional method. In particular, a production method using the hydroxyalkylbenzene as a solubilizing agent and the ketone represented by the general formula (2) as a dilution medium is particularly preferably exemplified. To be specific, such method of producing the pharmaceutical composition of the present invention is preferably a method involving: adding the hydroxyalkylbenzene to the compound represented by the general formula (1) or the salt thereof to solvate the compound or salt; and adding the ketone represented by the general formula (2) to dilute/solubilize the compound or salt. The solvation/solubilization process is performed preferably while heating to 30 to 90° C. The pharmaceutical composition of the present invention can be obtained by performing such processes and further treating the resultant product in accordance with a conventional method.

The pharmaceutical composition of the present invention may have any dosage form without particular limitation as long as the form is a form used for pharmaceutical compositions. Examples of the form include: oral administration preparations such as tablet, capsule, granule, film-coated agent, powder, and syrup; and parenteral administration preparations such as injection, suppository, inhalation, liniment, patch, aerosol, transdermal absorption agent, eyedrops, and nasal drops. Of those, skin preparations for external use such as liniment, patch, aerosol, and transdermal absorption agent are preferably exemplified. Preferred examples of the dosage form of the skin preparation for external use include lotion, emulsion, gel, cream, aerosol, nail enamel, and hydrogel patch. The lotion is particularly preferred.

The pharmaceutical composition of the present invention is preferably used for treatment of mycotic diseases or prevention of progression of the diseases by using characteristics of luliconazole or the like. For the mycotic diseases, there may be exemplified: tinea pedis such as athlete's foot; tinea corporis such as candida and pityriasis versicolor; and tinea on a hard keratin portion, such as tinea unguium. Because of remarkable effects, it is particularly preferred to use the pharmaceutical composition of the present invention for treatment of the hard keratin portion, such as tinea unguium. The effect of the pharmaceutical composition of the present invention is particularly suitably expressed on the nail, and such effect is also expressed on typical dermatomycosis. Therefore, a pharmaceutical composition for dermatomycosis, which satisfies the configuration of the present invention, also falls within the technical scope of the present invention. For such dermatomycosis, there may be exemplified tinea such as tinea pedis, or particularly hyperkeratotic tinea which appears on the heels or the like. It is preferred to apply the pharmaceutical composition of the present invention to hyperkeratotic tinea, on which the conventional medicaments hardly exert their effects, in the above-mentioned dermatomycosis, because the effect of the present invention is remarkably expressed.

The use aspect may be appropriately selected in consideration of patient's body weight, age, sex, symptom, etc. In the case of adults, the compound represented by the general formula (1) and/or the salt thereof is generally preferably administered in an amount of 0.01 to 1 g per day. In addition, the amount may be determined by reference to the amount of a compound represented by the general formula (1) and/or a salt thereof which is usually used for a disease caused by a fungus.

For example, the pharmaceutical composition for external use is applied to a diseased site one or several times a day at a preferred amount, and the treatment is preferably carried out day after day. In particular, for tinea unguium, luliconazole or the like as an effective component may be transferred into the nail in an amount that cannot be attained by a normal formulation. As a result, tinea unguium may be treated by simple external application without taking an antimycotic agent over a long period of time. In addition, recurrence and reinfection are being a major problem for tinea unguium. However, the recurrence and reinfection may be prevented by application of the pharmaceutical composition for external use of the present invention for 1 to 2 weeks after abatement of the symptom. The pharmaceutical composition of the present invention exerts a preventive effect in such a mode.

As described above, the pharmaceutical composition of the present invention may be a preparation component which has an effect of enhancing solubilization stability and steric stability of the compound represented by the general formula (1) and/or the salt thereof in low-temperature or high-temperature storage. The pharmaceutical composition of the present invention may be a preparation having the following properties 2) and 3). Further, when the compound represented by the general formula (1) and/or the salt thereof has a stereoisomer, the pharmaceutical composition may be a preparation having the following properties 1) to 3):

1) the amount of a stereoisomer of the compound and/or a salt thereof produced under a preservation condition of 40° C. or more for 3 weeks or more is 1% by mass or less, preferably 0.5% by mass or less with respect to the total mass of the compound and/or a salt thereof at the beginning;

2) no crystal is deposited when the preparation is preserved at 60° C. for 3 weeks;

3) no crystal is deposited when the preparation is preserved at 5° C. for 4 weeks.

The characteristic 1) may be determined by, for example, preserving a preparation at 40° C. for example, preferably at 60° C. for 3 weeks for example, preferably for 4 weeks after manufacture, performing liquid chromatography using an optically-active stationary phase which may separate a compound of interest from optical isomers thereof to optically resolve the compound from the optical isomers, and calculating the amount of the isomers by peak areas of the optical isomers in the resultant chart.

The characteristic 2) may be assessed by, for example, preserving a preparation at 60° C. for 3 weeks after manufacture, and observing the preparation with the naked eye and/or under a microscope. When no crystal deposition is confirmed with the naked eye and/or under a microscope, or a crystal is confirmed only with a microscope or through observation under a microscope and the time-dependent growth of the crystal is not confirmed, the assessment of no crystal deposition is given. (It should be noted that, hereinafter, such state may be referred to as "a small amount of crystal deposition was confirmed.")

The characteristic 3) may be assessed by, for example, preserving a preparation at 5° C. for 4 weeks after manufacture, and observing the preparation with the naked eye and/or under a microscope. When no crystal deposition is confirmed with the naked eye and/or under a microscope, or a crystal is confirmed only with a microscope or through observation under a microscope and the time-dependent growth of the crystal is not confirmed, the assessment of no crystal deposition is given. (It should be noted that, hereinafter, such state may be referred to as "a small amount of crystal deposition was confirmed.")

The thus-obtained pharmaceutical composition of the present invention has an excellent effect of maintaining its transparency over a long period of time although the composition contains a compound represented by the general formula (1) and/or a salt thereof in a high concentration. In addition, because crystal deposition after application is suppressed, inhibition of orientation and transfer of the compound to organs by the crystal is suppressed. Therefore, the composition has excellent bioavailability. Meanwhile, a sufficient amount of the compound is oriented to an organ with low drug orientation such as the nail, and hence the composition is preferred as a pharmaceutical composition for external use for the nail.

EXAMPLES

Hereinafter, the present invention is described in more detail by way of examples.

Example 1

According to the following formulation, a pharmaceutical composition 1 of the present invention was produced. That is, the formulation components were heated to 90° C. and stirred to solubilize the components, and the resultant mixture was cooled by stirring, thereby producing the pharmaceutical composition 1 of the present invention. In the same way as above, Comparative Examples 1 to 4 were prepared. These samples were stored at 40° C. for 1 month, and the amounts of the SE form, which is a stereoisomer of luliconazole produced, were determined under the following high-performance liquid chromatography conditions. The results are shown in Table 1. The results reveal that methyl ethyl ketone, which is the ketone represented by the general formula (2), has a similar ability for steric stabilization in storage at 40° C. for 1 month to that of propylene carbonate, N-methyl-2-pyrroridone (NMP), crotamiton, or DMSO.

Note that the structures of the SE form and the Z form, which are stereoisomers of luliconazole, are shown below.

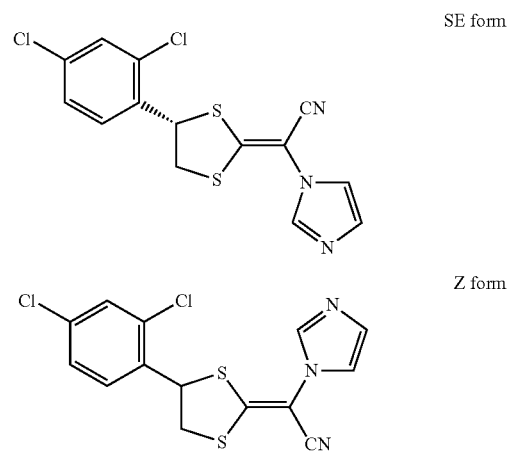

<Conditions of High-Performance Liquid Chromatography>

HPLC: LC-20AD, manufactured by Shimadzu Corporation

HPLC conditions: Column; CHIRALCEL OD-RH 4.6×150 mm,

Column temperature; 35° C.,

Mobile phase; a mixture of methanol/an aqueous solution of 1.8% potassium hexafluorophosphate (83:17, v/v), Flow rate; 0.56 mL/min., Detection; 295 nm

TABLE 1

| Components | Composition 1 | Comparative Example 1 | Comparative Example 2 | Comparative Example 3 | Comparative Example 4 (% by mass) |
|---|---|---|---|---|---|
| Luliconazole | 1 | 1 | 1 | 1 | 1 |
| Methyl ethyl ketone | 99 | | | | |
| Propylene carbonate | | 99 | | | |
| NMP | | | 99 | | |
| Crotamiton | | | | 99 | |
| DMSO | | | | | 99 |
| Total | 100 | 100 | 100 | 100 | 100 |
| SE form (%) | 0.15 | 0.22 | 0.16 | 0.14 | 0.35 |

Reference Example 1

According to the following formulation, a pharmaceutical composition 1 of Reference Example, and Comparative Examples 1 to 4 were prepared in the same way as in Example 1. A storage test was performed at 60° C. for 1 month, and the amounts of the SE form were determined. The results reveal that benzyl alcohol has a similar ability for steric stabilization in storage at 60° C. for 1 month to that of propylene carbonate, NMP, or crotamiton.

TABLE 2

|  | | | | | (% by mass) |
| --- | --- | --- | --- | --- | --- |
| Components | Reference Composition 1 | Comparative Example 1 | Comparative Example 2 | Comparative Example 3 | Comparative Example 4 |
| Luliconazole | 1 | 1 | 1 | 1 | 1 |
| Benzyl alcohol | 99 | | | | |
| Propylene carbonate | | 99 | | | |
| NMP | | | 99 | | |
| Crotamiton | | | | 99 | |
| DMSO | | | | | 99 |
| Total | 100 | 100 | 100 | 100 | 100 |
| SE form (%) | 1.0 | 1.11 | 0.24 | 0.11 | 4.33 |

Example 2

According to the following formulation, a pharmaceutical composition 2 of the present invention, and Comparative Example 5 were prepared in the same way as in Example 1. A storage test was performed at 60° C. for 1 month, and the amounts of the SE form were determined. The results reveal that methyl ethyl ketone, which is a ketone represented by the general formula (2), has a similar ability for steric stabilization in storage at 60° C. for 1 month to that of propylene carbonate, NMP, or crotamiton, even in the case of using ethanol as a dilution medium. In addition, in the case of using ethanol as a solvent, the steric stabilization effect was found to decrease compared with the case of using only methyl ethyl ketone as a solvent.

TABLE 3

|  | | (% by mass) |
| --- | --- | --- |
| Components | Composition 2 | Comparative Example 5 |
| Luliconazole | 1 | 1 |
| Methyl ethyl ketone | 5 | |
| Propylene carbonate | | |
| Dehydrated ethanol | 94 | 99 |
| Total | 100 | 100 |
| SE form (%) | 14.8 | 41.7 |

Examples 3 to 10

According to the following formulation described in Table 4, compositions 3 to 10 of the present invention were produced. Moreover, as Comparative Example 6, a compound was produced using diacetyl instead of the ketone represented by the general formula (2). Luliconazole and benzyl alcohol were mixed, and the ketone represented by the general formula (2) was added. The whole was heated to 90° C. to further dissolve the components, and the rest of the components were sequentially added, followed by stirring to solubilize the components. After the solubilization was confirmed, the solution was cooled by stirring, thereby obtaining a pharmaceutical composition. Moreover, the amounts of the SE form as well as the Z form were determined under the above-mentioned HPLC conditions. The results are shown in Table 4. The results reveal that the pharmaceutical compositions of the present invention each has ability to enable preparation of highly-concentrated preparations and to stabilize the steric structure and solubility of the compound represented by the general formula (1) and/or the salt thereof. Moreover, the data suggests that, in the case of addition of the ketone, a combination use with benzyl alcohol is preferred for both solubilization and steric stabilization. Such combination was found to provide an excellent effect of stabilizing the steric structure even in the case of using ethanol as a solvent. As the concentration of luliconazole becomes higher, the effect becomes more significant. Therefore, the concentration of luliconazole is preferably 4% by mass or more, or particularly preferably 5% by mass or more.

TABLE 4

|  | | | | | | | | | (% by mass) |
| --- | --- | --- | --- | --- | --- | --- | --- | --- | --- |
|  | Comp. 3 | Comp. 4 | Comp. 5 | Comp. 6 | Comp. 7 | Comp. 8 | Comp. 9 | Comp. 10 | Comparative Example 6 |
| Luliconazole | 8 | 10 | 12 | 8 | 10 | 12 | 10 | 15 | 10 |
| Methyl ethyl ketone (2-butanone) | 10 | 10 | 10 | | | | | | |
| Methyl isobutyl ketone (4-methyl-2-pentanone) | | | | 10 | 10 | 10 | | | |
| Benzophenone | | | | | | | 10 | 10 | |
| Diacetyl | | | | | | | | | 10 |
| Benzyl alcohol | 2 | 2 | 2 | 2 | 2 | 2 | 2 | 4 | 2 |
| Lactic acid | 6 | 6 | 8 | 6 | 6 | 8 | 6 | 8 | 6 |
| Propylene carbonate | 3 | 5 | 5 | 3 | 5 | 5 | 5 | 5 | 5 |
| Propylene glycol | 10 | 10 | 10 | 10 | 10 | 10 | 10 | 10 | 10 |
| Dehydrated ethanol | 61 | 57 | 53 | 61 | 57 | 53 | 57 | 43 | 57 |
| Total | 100 | 100 | 100 | 100 | 100 | 100 | 100 | 100 | 100 |
| Presence or absence of precipitation | | | | | | | | | |
| At production time | ○ | ○ | ○ | ○ | ○ | ○ | ○ | ○ | ○ |
| At starting time | ○ | ○ | ○ | ○ | ○ | x | ○ | ○ | ○ |
| 5° C., 1 week | ○ | ○ | x | ○ | ○ | x | ○ | ○ | ○ |
| 5° C., 1 month | ○ | ○ | x | ○ | ○ | x | ○ | ○ | ○ |
| (60° C., 3 weeks) | ○ | ○ | ○ | ○ | ○ | ○ | ○ | ○ | ○ |

TABLE 4-continued

|  | Comp. 3 | Comp. 4 | Comp. 5 | Comp. 6 | Comp. 7 | Comp. 8 | Comp. 9 | Comp. 10 | (% by mass) Comparative Example 6 |
|---|---|---|---|---|---|---|---|---|---|
| Stability |  |  |  |  |  |  |  |  |  |
| At starting time |  |  |  |  |  |  |  |  |  |
| Quantification (based on the value at the starting time) (%) | 100 | 100 | 100 | 100 | 100 | 100 | 100 | 100 | 100 |
| Purity SE form (%) | 0.23 | 0.23 | 0.23 | 0.24 | 0.23 | 0.24 | 0.22 | 0.23 | 0.24 |
| Z form (%) | 0.03 | 0.03 | 0.03 | 0.03 | 0.03 | 0.02 | 0.03 | 0.03 | 0.06 |
| Others (%) | 0.03 | 0.03 | 0.03 | 0 | 0.02 | 0.02 | 0 | 0 | 0 |
| 60° C., 3 week |  |  |  |  |  |  |  |  |  |
| Quantification (based on the value at the starting time) (%) | 100.3 | 100.7 | 100.4 | 101 | 100.2 | 107 | 99.5 | 99.8 | 81.1 |
| Purity SE form (%) | 0.26 | 0.23 | 0.27 | 0.26 | 0.27 | 0.29 | 0.25 | 0.26 | 0.19 |
| Z form (%) | 0.08 | 0.08 | 0.09 | 0.07 | 0.08 | 0.09 | 0.08 | 0.1 | 0.12 |
| Others (%) | 0.11 | 0.16 | 0.2 | 0.12 | 0.16 | 0.2 | 0.2 | 0.31 | 0.48 | o: No precipitation
x: Precipitation visible to the naked eye

INDUSTRIAL APPLICABILITY

The present invention can be applied to pharmaceutical compositions.

What is claimed is:

1. A pharmaceutical composition consisting of:
   1) 5 to 10% by mass with respect to the total amount of the pharmaceutical composition of luliconazole having the chemical name of (R)-(−)-(E)-[4-(2,4-dichlorophenyl)-1,3-dithiolan-2-ylidene]-1-imidazolylacetonitrile represented by the following general formula (1) and/or a salt thereof;
   2) 10 to 80% by mass with respect to the total amount of the pharmaceutical composition of a ketone represented by the following general formula (2);
   3) a hydroxyalkylbenzene;
   4) lactic acid;
   5) propylene carbonate;
   6) polyvalent alcohol;
   7) ethanol, and optionally
   8) phosphoric acid,
   Wherein mass ratio of the ketone represented by the general formula (2) and the hydroxyalkylbenzene is 20:1 to 1:1:

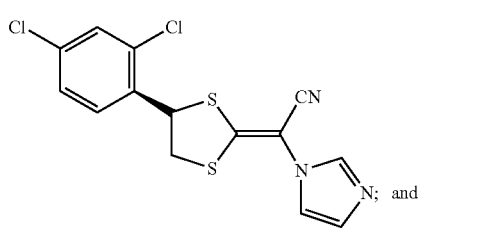

General formula (1)

General formula (2)

where R3 and R4 each independently represents an alkyl group, alkenyl group, alkyl group having an aromatic group, alkenyl group having an aromatic group, or an aromatic group, and wherein a sum of a number of carbon atoms in R3 and R4 is 3 or more.

2. The pharmaceutical composition according to claim 1, wherein the ketone represented by the general formula (2) is methyl ethyl ketone, methyl isobutyl ketone, or benzophenone.

3. The pharmaceutical composition according to claim 1, wherein the hydroxyalkylbenzene is benzyl alcohol.

4. A method for treating tinea unguium comprising treating an individual in need of treatment with the pharmaceutical composition of claim 1.

5. A method of producing the pharmaceutical composition according to claim 1, comprising:
   mixing, as a solubilizing agent, the hydroxyalkylbenzene with the compound represented by the general formula (1) and/or the salt thereof; and
   mixing, as a dilution medium, the ketone represented by the general formula (2) with the resultant mixture.

6. The method according to claim 4, wherein the ketone represented by the general formula (2) is methyl ethyl ketone, methyl isobutyl ketone, or benzophenone.

* * * * *